United States Patent
Dearnaley

(10) Patent No.: US 7,252,684 B2
(45) Date of Patent: Aug. 7, 2007

(54) CERAMIC IN REPLACEMENT COMPONENTS

(75) Inventor: Geoffrey Dearnaley, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/288,312

(22) Filed: Nov. 6, 2002

(65) Prior Publication Data

US 2004/0088052 A1 May 6, 2004

(51) Int. Cl.
*A61F 2/02* (2006.01)
*A61F 2/28* (2006.01)
*B05D 3/00* (2006.01)

(52) U.S. Cl. .................................. 623/16.11
(58) Field of Classification Search ............. 623/16.11, 623/18.11, 23.36, 23.4, 23.56, 23.57, 22.15, 623/22.23, 23.58, 23.6, 23.61, 23.71, 926; 424/423, 424; 427/2.26, 2.27, 523, 525, 427/527
See application file for complete search history.

(56) References Cited

U.S. PATENT DOCUMENTS

| | | | | |
|---|---|---|---|---|
| 5,496,374 A | * | 3/1996 | Blanchard et al. | 424/423 |
| 5,593,452 A | | 1/1997 | Higham et al. | 623/23 |
| 5,731,045 A | * | 3/1998 | Dearnaley et al. | 427/527 |
| 6,010,533 A | | 1/2000 | Pope et al. | 623/18 |
| 6,046,758 A | * | 4/2000 | Brown et al. | 347/203 |
| 6,120,545 A | | 9/2000 | Hamelijnck et al. | 623/22.15 |
| 6,171,343 B1 | | 1/2001 | Dearnaley et al. | 623/23.6 |
| 6,217,615 B1 | | 4/2001 | Sioshansi et al. | 623/18.11 |
| 6,290,726 B1 | | 9/2001 | Pope et al. | 623/22.15 |
| 6,306,175 B1 | | 10/2001 | Dearnaley et al. | 623/23.11 |
| 6,312,472 B1 | | 11/2001 | Hall et al. | 623/23.53 |
| 6,447,295 B1 | * | 9/2002 | Kumar et al. | 433/172 |
| 2004/0028906 A1 | * | 2/2004 | Anderson et al. | 428/408 |

OTHER PUBLICATIONS

"Strengthening of $Al_2O_3$ by Ion Implantation", T. Hioki, A. Itoh, S. Noda, H. Doi, J. Kawato and O. Kamigaito; Toyota Central Research & Development Laboratories, Inc., pp. 1-12.
"The Effects of Ion Implantation on the Structure of Ceramics", Carl J. McHargue, Journal of Mineral Metal and Material Society, vol. 43(7), Jul. 1991, pp. 40-44.
"Changing the Surface Mechanical Properties of Silicon and $\alpha$-$Al_2O_3$ by Ion Implantation", P.J. Burnett, T.F. Page, Journal of Materials Science 19 (1984), 1984 Chapman and Hall Ltd., pp. 3524-3545.
"The Friction and Hardness of Ion-Implanted Sapphire", P.J. Burnett and T.F. Page, Wear, vol. 114 1987, pp. 85-96.

(Continued)

*Primary Examiner*—David J. Isabella
(74) *Attorney, Agent, or Firm*—Grossman, Tucker, Perrault

(57) ABSTRACT

A method and apparatus for a prosthesis. At least a portion of the prosthesis is made from a ceramic that is treated with ion implantation, which causes a controllable, bilateral compressive stress of the ceramic. A diamond-like-coating (DLC) can be coated on the ceramic and in the same chamber as the ion implantation. After treating by ion implantation and coating with DLC, the ceramic will be strengthened and have a low coefficient of friction and thereby be made much less likely to fracture under load.

20 Claims, 3 Drawing Sheets

OTHER PUBLICATIONS

"*Criteria for Mechanical Property Modifications of Ceramic Surfaces By Ion Implantation*", P.J. Burnett and T.F. Page, Radiation Effects, (1986), vol. 97, pp. 282-296.

"Mechanical Property Changes in Sapphire by Nickel Ion Implantation and their Dependence on Implantation Temperature", Hioaki A. Itoh, et al., Journal of Materials Science 21, (1986), pp. 1321-1328.

"Modification of the Mechanical Properties of Ceramic Surfaces by Energetic Ion Irradiation", Wolfgang Bolse and Stathis D. Peteves, Nuclear Instruments and Methods in Physics Research B68, (1992), pp. 331-341.

* cited by examiner

CERAMIC IN REPLACEMENT COMPONENTS

BACKGROUND OF THE INVENTION

1. Field of the Invention

The present invention generally relates to ceramics. More specifically, a method of improvement of ceramics in replacement components, such as components in hip and knee replacements.

2. Description of the Related Art

It's inevitable that all living things age overtime, so do the many components that make up the living things. Human beings are also living things and we have the ability to regenerate some of our components when they wear out or some of the components are just naturally replaced. For example, our skin cells are continuously replaced on a daily basis, hair cells are continuously added so that hair can grow, and calcium is continuously absorbed and reabsorbed in bone components. The absorption of calcium in the bones helps to strengthen them. However, because of aging, degenerative diseases, such as osteoporosis, or other causes, the bones can become fragile and break causing excruciating pain. In other cases, as in osteoarthritis, the cartilage becomes worn away and bone deformities develop. The load-bearing situation on bone-on-bone is very painful. In addition, primarily in younger patients, sports-related injuries can lead to severe damage to hips or knees, necessitating surgery.

For many years, man-made devices have been developed in order to help replace components that cannot be regenerated and are no longer functioning properly. Such man-made devices include biocompatible devices and materials. The devices include heart valves, pace makers, spinal, dental, or breast implants, collagen for soft tissue augmentation, and orthopedic devices, such as total knee and hip joint replacements.

Artificial joints can include a plastic-cup made of ultra-high molecular weight polyethylene (UHMWPE) that is placed in a joint socket, a metal (titanium alloy or cobalt chromium alloy) or ceramic (aluminum oxide or zirconium oxide) ball that is complementary to the cup and is affixed to a metal stem. These artificial joints are used to replace hip, knee, shoulder, and other joints in order to restore function after degeneration, car and construction accidents, and sport injuries.

However, these artificial joints typically do not last, as long as needed, especially when the patient is young and can typically live longer due to medical advancements. Conventional artificial joints last about 10 years and need to be replaced due to wear and loosening. Additionally, due to localized stress from the interaction of the ball and socket, small particles can break off from the surface and contaminate the surrounding synovial fluid. The body's immune system will attempt to degrade the particles by secreting enzymes, which can kill the adjacent bone cells or cause osteolysis and lead to mechanical loosening and failure of the artificial joints. Further, despite the best efforts and techniques (including polishing), the surfaces of the balls can have protuberances, which through use can cause scratches that lead to microcracks in the balls and ultimately to catastrophic fracture of the ball and joint. These fractures can be extremely painful to the patients and require expensive replacements and surgery. The more expensive ceramic joint replacements are normally fitted in younger, more active patients, in the expectation that the life of the joint replacement will be longer than that of metallic components. This has too often not been the case, principally due to fracture of the more brittle ceramic.

Therefore, there is a need for a method and means to decrease particles in the synovial fluids caused by friction on the ceramics. There is also a need to prevent microcracks from starting or prevent the microcracks from increasing in size, thereby increasing the life of the ceramic prosthesis.

SUMMARY OF THE INVENTION

The present invention generally provides for a method and apparatus to strengthen the ceramic portion of a prosthesis. In one embodiment, a method of strengthening a prosthesis is provided and can include treating at least a ceramic portion of the prosthesis with a first ion beam implantation, and coating at least the ceramic portion with a diamond-like-coating. The treating and the coating can be accomplished in the same vacuum chamber. Treating at least the ceramic portion of the prosthesis with ion implantation can cause a controlled compressive stress in the ceramic. The at least ceramic portion can be treated by ion implantation with ions in a vacuum at a dose and energy sufficient to cause the controllable compressive stress and not cause the at least ceramic portion to become amorphous. Coating can further include exposing the at least ceramic portion of the prosthesis to a vacuum, condensing a diamond-like-carbon precursor, and bombarding with the diamond-like-carbon precursors with a second ion beam. The energy of the first ion beam used in the treating may be between 30-130 keV or between 50-100 keV. The energy of the second ion beam used in the coating may be between 5-100 keV or between 10-30 keV.

In another embodiment, a method of hardening a prosthesis can include treating a ceramic portion of the prosthesis with an ion beam implantation with ions in a vacuum at a dose and energy sufficient to cause the controllable compressive stress and not cause the ceramic to become amorphous. The ceramic can be treated with 30-130 keV or with 50-100 keV of energy from the ion beam. The ceramic can also be treated with ions having a dose of about $10^{17}$ ions per $cm^2$ or less and the ion may be helium. The ceramic can be selected from Alumina ($Al_2O_3$), Zirconia, Chromium Oxide, $Cr_2O_3$, Silicon Oxide ($SiO_2$), other ceramics, or metals coated with one of the said ceramics and a combination thereof or metals coated with one of the said ceramics.

In still another embodiment, a prosthesis is provided and can include a ceramic treated with ion implantation that can cause a controllable compressive stress, and a diamond-like-coating on the ceramic, said diamond-like-coating can have a low friction coefficient. The ceramic may be on a ball portion of the prosthesis or a cup portion of the prosthesis. The ceramic can be positioned in locations such as joints, knees, fingers, toes, shoulders, arms, elbows, hips, ankles, necks, spinal cord, other a combination thereof. The controllable compressive stress may be a maximum bilateral compressive stress. The ceramic can be treated and coated in the same vacuum chamber. The ceramic can be treated with 30-300 keV or with 50-100 keV of energy from the ion beam. Additionally, the ceramic can be coated with 5-100 keV or with 10-30 keV of energy from the ion beam. The ceramic can also be treated by ion implantation with ions in a vacuum at a dose and energy sufficient to cause the controllable compressive stress and not cause the ceramic to become amorphous. The ceramic can be Alumina ($Al_2O_3$), Zirconia, Chromium Oxide, $Cr_2O_3$, Silicon Oxide ($SiO_2$), other ceramics, and a combination thereof. The ceramic can be treated with ions having a dose of about $1\times10^{17}$ ions per cm² or less and the ion may be helium. The ion can also be selected from positive ions, nitrogen ions, calcium ions, hydrogen ions, helium ions, boron ions, other ions, and a combination thereof.

In still another embodiment, the prosthesis apparatus can include a prosthesis having at least a portion made from ceramic treated by ion implantation with ions in a vacuum at a dose and energy sufficient to cause a controllable compressive stress and not cause the ceramic to become amorphous. The ceramic is on a ball portion and/or a cup portion of the prosthesis. The ceramic can be positioned at joints, knees, fingers, toes, shoulders, arms, elbows, hips, ankles, necks, spinal cord, other a combination thereof. The ceramic can be treated with 30-300 keV or 50-100 keV of energy from the ion beam. The prosthesis apparatus can further include a diamond-like-coating on the ceramic portion of the prosthesis.

BRIEF DESCRIPTION OF THE DRAWINGS

So that the manner in which the above recited embodiments of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

The embodiments of the present invention relates to a method and apparatus to increase the life of the artificial joints, such as hip, shoulder, fingers, toes, arms, elbows, ankles,-necks, spinal cord, knee replacements and other joint replacements. The application of the present invention is not limited to humans, rather it can be used in dogs, cats, monkeys, elephants, and other animals. The application can be used in load-bearing or non-load-bearing surfaces or prosthesis, which may be manufactured wholly or partially from ceramic materials.

Figure 1:
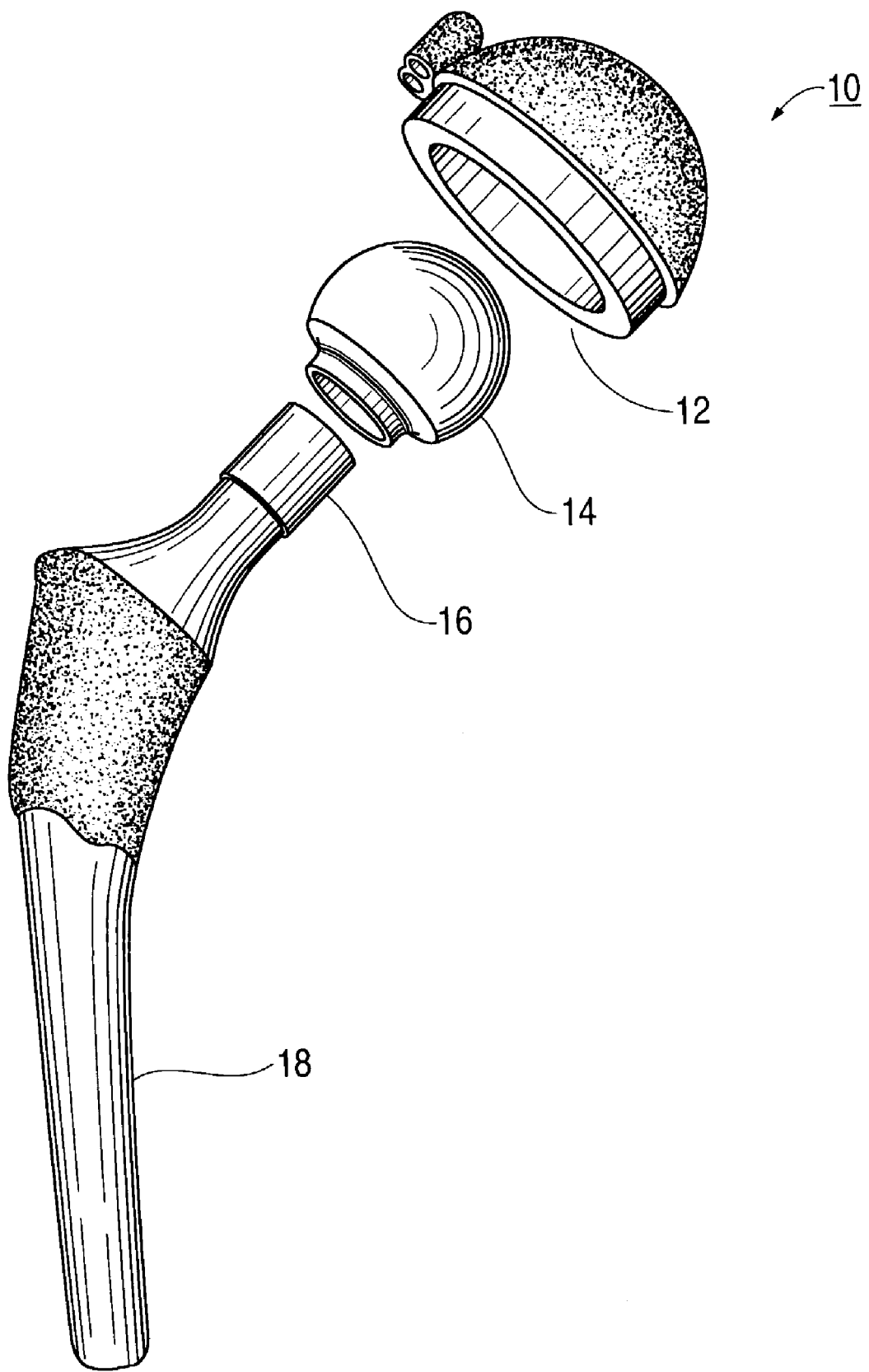
FIG. 1 illustrates an artificial hip and joint system.

FIG. 1 illustrates an artificial hip and joint system 10. The system 10 can include a hemispherical socket 12 or an acetabular cup, a spherical ball 14 that can be attached to a femoral head 16 and a femoral stem 18. The socket 12 is typically made from a metal and is lined with UHMWPE or other materials. The lining is designed to decrease the friction between the socket 12 and the ball 14.

The ball 14, which is adapted to fit into the socket 12, can be made from ceramics. Some possible ceramics can include Alumina ($Al_2O_3$), Zirconia, Chromium Oxide, $Cr_2O_3$, Silicon Oxide ($SiO_2$), and others that can be adapted for use in vivo. The ball 14 can be constructed and arranged to mate with the femoral head 16, which is part of the femoral stem 18. The femoral stem 18 can be implanted into existing long bone that may still be functional or can be used as the long bone, if none is available.

Although the liner is designed to reduce friction between the socket 12 and the ball 14, over time, the liner and the ceramic can wear away due to the reciprocating motion causing minute particles to be introduced in the body and causing osteolysis. Additionally, the ceramic, even after extensive polishing to remove any surface protuberances, may still have small amounts of protuberances therein. Additionally, the ceramic may inherently contain microcracks or microfractures (see FIG. 3A) or friction acting on the protuberances can cause microcracks in the ball 14, both of which can lead to catastrophic failure of the ball by fracture.

In one embodiment of the invention, an ion implantation process can be used to decrease the amount of microcracks produced by friction, to stop further migration of microcracks and to close at least a portion of the microcracks. At the right conditions, ion beam implantation will induce a controlled bilateral compressive stress on the ceramics, thereby strengthening it.

Ion implantation is a process that can modify near surface regions of a work piece, such as ceramic balls, without increasing the dimensions, changing the finish or causing thermal distortion. Ion implantation uses energy beams of ions, such as low energy, high energy, direct-beam, and plasma immersion ion implantation.

Figure 2:
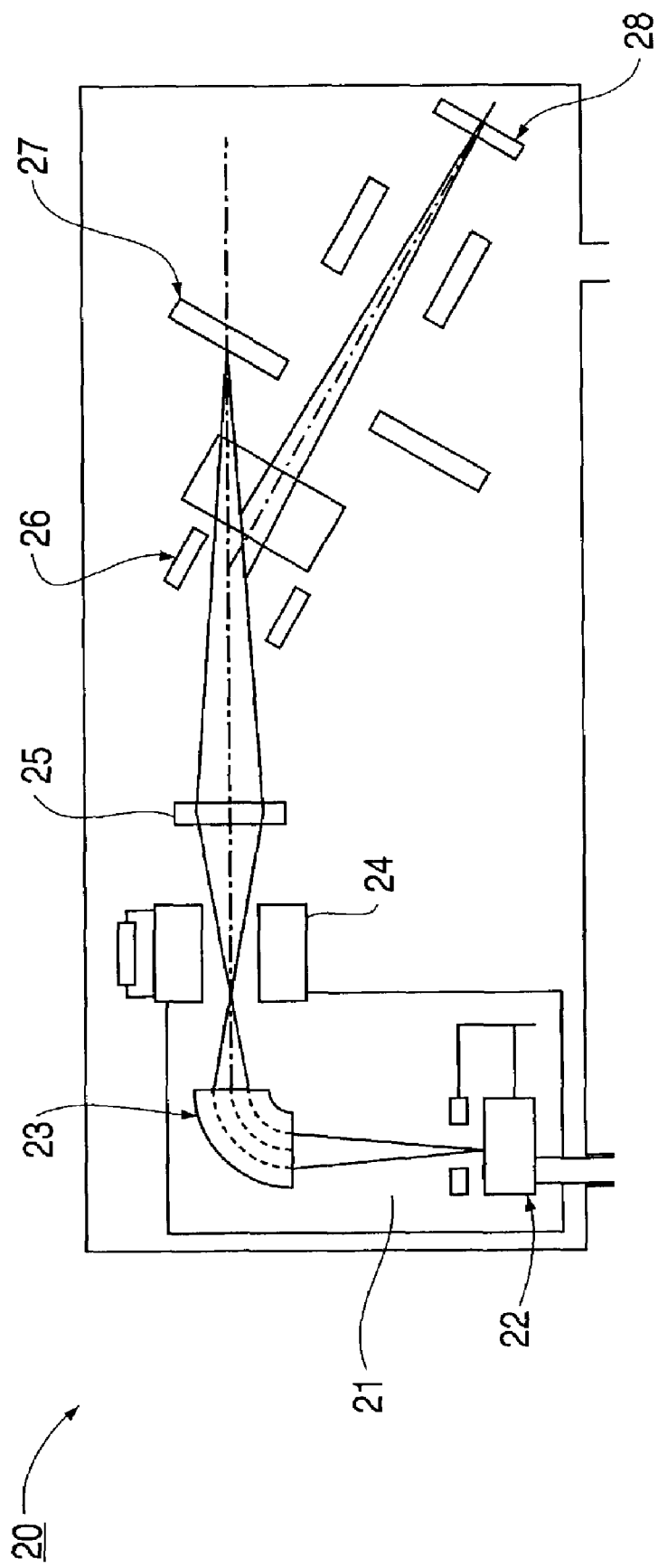
FIG. 2 is an illustration of an ion implantation system.

FIG. 2 is an illustration of an ion implantation system 20. The system 20 includes a chamber 21 that contains an ion source 22, an analyzing magnet 23, an acceleration tube 24, a focus device 25, a neutral beam trap and beam gate 26, a second beam trap and gate plate 27, and a work piece holder 28. The chamber 21 is maintained at low pressure or a vacuum around $1\times10^{-3}$ to about $1\times10^{-7}$ Torr. The ion source can be a gas or a solid source. The ions used herein are positive ions, such as nitrogen ions, calcium ions, hydrogen ions, boron ions, other ions and preferably helium ions. Negatively charged electrons traveling from a filament to an anode collide within the ion source to create positively charged ions used in ion implantation.

The analyzing magnet 23 creates a magnetic field, where the positively charged ions are bent into an arc with a certain radius. The parameters of the ions that the magnet 23 analyzes are mass, speed, and charge in order to select the desired ions. The magnet 23 allows only the desired species with the specific parameters to exit from an opening provided therein. The acceleration tube 24 accelerates the ions exiting from the magnet 23 to the desired velocity in order to penetrate the work piece. The focus device 25 uses magnetic lenses to focus the beam exiting from the tube 24 into a smaller beam for better implantation. The traps and gates 26 and 27 remove any neutral ions that may be present in the beam by directing the positive ions in another direction and away from the neutral ions. The traps and gates 26 and 27 can direct the positive ions towards the work piece holder 28, which can hold the work piece, such as a prosthesis piece or the ball 14. The work piece holder 28 can include a jig capable of holding a multiplicity of ceramic components and designed to allow the angle of incidence of the ion beam on the components to be varied, continuously or discontinuously, during ion implantation.

In operation, the desired prosthetic portion or the ball 14 portion of the hip and joint system 10 can be placed in the chamber 21 for ion implantation. The ball 14 is held in position by the work piece holder 28. Helium is the preferred ion in the ion implantation process. Helium can be used in the ion implantation process because of its lower molecular weight, and because it can be easily used with conventional industrial ion implantation system 20, with energies around 30 keV-500 keV. Other ions, such as argon or nitrogen, can also be used but can require a Cockcroft-type ion accelerator (high-end research accelerator) to provide the necessary energies for the desired penetration. Because helium produces displacements towards the end of the ion range within the ceramic, in order to achieve a more uniform compressive stress distribution, it is necessary to vary the ion energy, continuously or discontinuously, during irradiation by about a factor of four (e.g. from 25 keV to 100 keV).

Once the ball 14 is held in position, the ceramic is strengthened by ion implantation. Preferably, the energy level can be around 30-300 keV, and more preferably around 50-100 keV, with about $1\times10^{17}$ ions per cm$^2$ or less. Beyond $1\times10^{17}$ ions per cm$^2$, the ceramic may become amorphous. If the ceramic becomes amorphous, then the desired maximum compressive stress state is not achievable. As the helium travels into the ceramic, it causes radiation damage (recombination of vacancies and interstitials) and displaces the targeted atoms from their lattice positions due to the volume expansion. The displacement of the targeted atoms can produce a large amount of controllable compressive stress on the ceramic, which makes the ceramic stronger. Helium has the property in solid materials of being highly insoluble, and of stabilizing clusters of atomic vacancies around the helium atom. In this way, it is capable of reducing the recombination of the said vacancies with interstitials, produced in equal numbers during ion irradiation.

The stress is controllable because the ion implantation parameters can be changed (increase or decrease energy levels, type of ions, such as heavyweight or lightweight, etc.), so that the compressive stress is at any compression stress state that is desired. The desired state can be dependent on the amount of stress that would be anticipated in the prosthesis. For example, in a ball for a hip replacement, where the stress is great, more compressive stress is needed, while in a ball that may be in a finger joint, less compressive stress is needed. Because the ceramic is stronger, the microcracks that can be caused through friction is prevented. Additionally, the ion beam should at least penetrate, as far as, the depth of the microcracks to be the most effective.

Figure 3A:
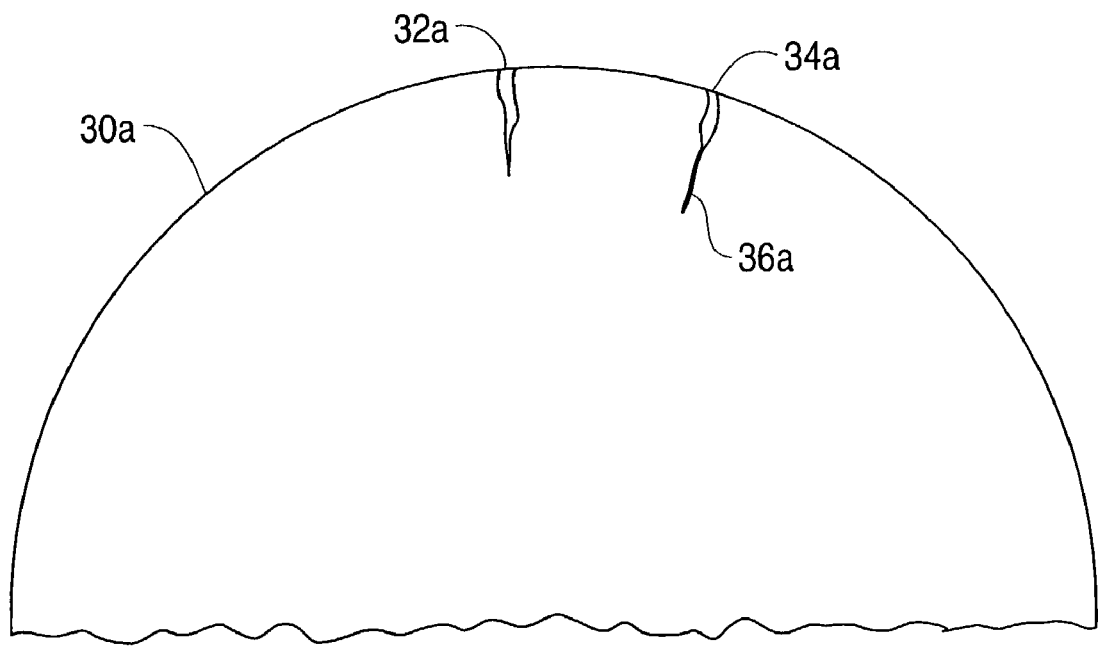
FIG. 3A illustrates an enlarged view of microcracks that can occur in ceramic balls.

FIG. 3A illustrates an enlarged view of microcracks that can occur in ceramic balls. A ball 30a is illustrated having microcracks 32a and 34a. The microcracks 32a and 34a are typical microcracks that can occur at the surface of the ceramic ball. Even after high speed polishing, the microcracks 32a and 34a can still be present. Microcrack 34a has a large tail portion 36a, which if left untreated, can produce a catastrophic failure of the ceramic ball under load conditions. With the use of ion implantation, the microcracks 32a and 34a can decrease in size or be prevented from further propagation.

Figure 3B:
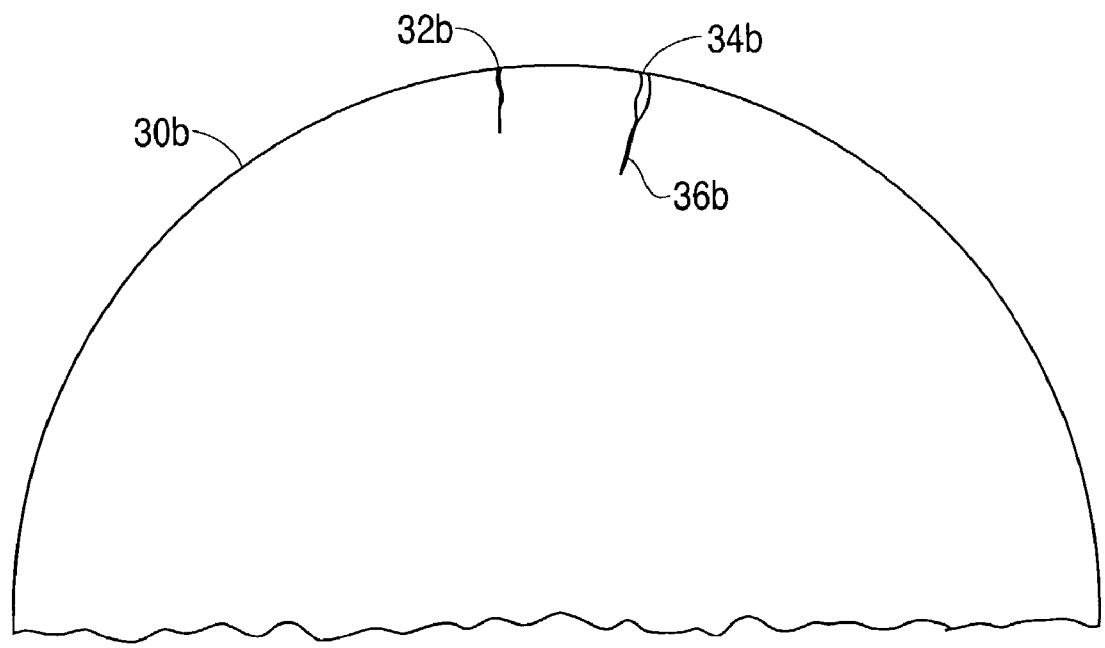
FIG. 3B illustrates the microcracks after ion implantation.

FIG. 3B illustrates the microcracks after ion implantation. The ball 30b has microcracks 32b and 34b on its surface that corresponds to microcracks 32a and 34a in FIG. 3A. The ion implantation can decrease the size of the microcracks or close up to the microcracks due to the displacement of the target atoms by the helium being implanted. As shown in FIG. 3A, the microcrack 32b has been substantially closed-up. Due to the ion implantation on the ball 30b, microcrack 34b and its tail 36b have been prevented from expanding or traveling further. The maximum compressive stress induced in the surface region of the ceramic counteracts the applied tensile stress due to loading and to friction between load-bearing surfaces and prevents the ceramic atoms from moving, thus, the ceramic microcracks are prevented from increasing or spreading. Because the microcracks 32b, 34b and 36b are prevented from expanding or traveling, this will reduce the likelihood of a catastrophic failure of the ball 30b.

It should be noted that the preferred parameters of the energy level, the amount per cm$^2$ of the ion beam should be appropriate for the particular ion used to penetrate to the desired depth and should not be so high that the ceramic becomes amorphous. As stated above, other ions can be used, such as nitrogen (does not stabilize vacancy-type defects, as well as helium), neon and argon (which have limited penetrating power) and hydrogen (which has a low efficiency for producing radiation damage in ceramic materials).

Although it is preferable, it is not required that the ion beam be utilized on all parts of the ceramic. In order to save time, materials, and costs, all the surfaces of the ceramic ball or the desired ceramic prosthesis do not have to be treated. The ceramic can be treated in the areas that are affected by friction, load-bearing surfaces or where the microcracks occur.

By using the ion beam implantation, the ceramics that are used in prosthesis can be strengthened by increasing the compressive stress. Microcracks that are present in the ceramic of the prosthesis can be prevented from spreading, can be reduced in size, and microcracks associated with surface flaws, such as from protuberances, can be reduced or prevented. Ion beam implantation can provide an easy, cost-effective method to strengthen ceramics for use in prosthesis. Additionally, the ion beam also "cleans" the treated surface of the ceramic by sputtering so that no additional cleaning is required, should the ceramic undergo additional processing, such as coating.

One such additional process in another embodiment of the present invention can be applying a diamond-like carbon ("DLC") coating to the ceramics to reduce the friction between the prosthesis, such as the ball and cup. DLC provides a low friction, high hardness, and chemically inert (biocompatible) coating to ceramics. DLC is an amorphous solid comprising a highly cross-linked carbon network with a high degree of sp$^3$ bonding that provides similar characteristics of diamonds. DLC may be deposited by a variety of techniques centered on energetic ion bombardment, such as plasma assisted chemical vapor deposition (CVD), ion beam assisted sputtering, radio frequency (RF) plasma-assisted CVD, cathodic arc and laser ablation of carbon targets.

DLC depositing typically is a three-step process. In step one, the surface of the work piece, such as a metal ball, that is to be coated with DLC, is cleaned with argon ions in a vacuum to remove any contaminants. In step two, the metal ball is heated so that a bonding material, such as silicon or titanium, is deposited by ion assisted beam to the metal ball to form a metal-silicon bond. In step three, an ion beam assisted deposition of DLC is used to form a silicon-DLC bond. These steps are applied to metal prosthesis. However, DLC can be coated on ceramics without the binding material.

In one embodiment of the invention, a ceramic prosthesis that was previously treated by ion-implantation (as discussed above) is coated with DLC. Ceramic coated with DLC provides a lower coefficient of friction (<0.1) when interacting with UHMWPE, as compared to metal when coated with DLC interacting with UHMWPE (0.14), and is favored especially in the ball portion. Steps one and two can be eliminated if the surface has been previously cleaned by the above-mentioned ion implantation process and the DLC is applied directly on the ceramic prosthesis, without the need of the bonding material. The DLC can be deposited on the ceramic prosthesis in the same vacuum chamber that was previously used for ion implantation, without the need of another separate chamber for depositing DLC.

A DLC precursor is deposited on the previously ion implanted ceramic prosthesis with the assistance of ion beam implantation. The ceramic prosthesis is cooled down below 100° C. to allow the DLC precursor to condense onto the ceramic. In a preferred embodiment, the DLC precursor is polyphenyl ether or penta-phenyl-trimethyl siloxane, however, other suitable precursor materials include carbon-based diffusion pump materials, which have a low vapor pressure and can be vaporized stably at room temperature. Preferable diffusion pump fluids can include polydimethyl siloxane and elcosyl napthalene.

The precursor is vaporized and condensed onto the surface of the ceramic prosthesis using known methods. The precursor is vaporized by being placed in a heated reservoir and heated to about 140° C.-180° C. and the vapors are directed onto the cooled component. Simultaneously, the ceramic should be bombarded, either in a continuous or interrupted fashion, with an energetic beam of ions. The preferred ion source is nitrogen, but other ions can include argon, hydrogen, silicon, methane, helium and neon. The ion beam should be between about 5 keV to 100 keV, preferably between about 10-30 keV. The ion beam bombardment helps to rupture about 80% of the carbon-hydrogen bonds in the precursor, in order to form a non-crystalline coating of amorphous carbon. The ion beam strongly enhances adhesion of the DLC coating by rupturing and subsequently reforming inter-atomic bonds across the interfaces. The preferred thickness of the DLC should between about 100 nm-1 micron.

The DLC provides the ceramic with a coating having a low coefficient of friction so that damage from tensile stresses caused by friction is minimized. DLC also provides a strong coating that increases wear resistance and increases the life of the prosthesis. The coating helps to decrease surface microcracks that can be caused by friction. DLC is cheaper to use than actual polycrystalline diamond components because it's synthetic, but still provides similar characteristics as the diamond. By ion implanting to increase compressive stress and depositing DLC in the same chamber, throughput of the ceramic prosthesis is increased. Additionally, the production time and costs are decreased due to the elimination of at least two steps in the deposition of DLC.

The embodiments of the invention provide for a method to control the compressive stress present in the ceramic. Once the desired compressive stress is achieved in the ceramic, then the ceramic's strength can be at its maximum capacity. After ion implantation, DLC coating can be applied to the ceramic. With the ion implantation and the DLC coating, the ceramic will be resistant to microcracks and scratches and thus, will have a longer useful life. By having a longer useful life, the ceramic prosthesis will not have to be replaced as often as conventional prosthesis. It will be recognized by a person skilled in the art that the implantation and/or the DLC coating can be applied to all load-bearing surfaces used in the prosthesis, including the ball and socket.

While the foregoing is directed to embodiments of the present invention, other and further embodiments of the invention may be devised without departing from the basic scope thereof, and the scope thereof is determined by the claims that follow.

The invention claimed is:

1. A prosthesis, comprising:
   a prosthetic joint comprising a ball portion and a cup portion said ball portion having an outer load bearing surface configured to engage with a load bearing surface within said cup portion;
   a ceramic treated with ion implantation, wherein said ion implanted ceramic is characterized as having a compressive stress in said surface due to said ion implantation wherein said ion-implanted ceramic with said compressive stress is not amorphous, wherein said ion implanted ceramic is said load bearing surface on at least one of said ball portion and said cup portion of said prosthetic joint; and
   a diamond-like coating on the ceramic load bearing surface, said diamond-like coating comprising an amorphous and cross-linked carbon network and wherein said diamond-like coating includes inter-atomic bonds between said ceramic and said diamond like coating.

2. The prosthesis of claim 1 wherein said ion implanted ceramic is on said ball portion of said prosthetic joint.

3. The prosthesis of claim 1 wherein said ion implanted ceramic is on said cup portion of said prosthetic joint.

4. The prosthesis of claim 1 wherein said ball and said cup portion each including load bearing surfaces defining a tensile stress, wherein at least one of said ball and said cup portions comprises said ion implanted ceramic having said compressive stress sufficient to counteract said tensile stress.

5. The prosthesis of claim 1 wherein said ion-implanted ceramic is further characterized as having a maximum compressive stress in said surface due to said ion implantation wherein said ceramic with said maximum compressive stress is not amorphous.

6. The prosthesis of claim 1, wherein the prosthetic joint comprises a knee joint, a finger joint, a toe joint, a shoulder joint, an arm joint, an elbow joint, a hip joint, an ankle joint, a neck joint, a spinal cord joint, and a combination thereof.

7. The prosthesis of claim 1, wherein the ceramic is selected from a group consisting of Alumina ($Al_2O_3$), Zirconia, Chromium Oxide ($Cr_2O_3$), Silicon Oxide ($SiO_2$) and a combination thereof.

8. The prosthesis of claim 1, wherein the ceramic treated with ion implantation comprises a ceramic treated at a concentration of about $1 \times 10^{17}$ ions per $cm^2$ or less.

9. The prosthesis of claim 1, wherein the ion implanted in said ceramic is selected from a group consisting of positive ions, nitrogen ions, calcium ions, hydrogen ions, boron ions, and a combination thereof.

10. A prosthesis, comprising:
    a prosthetic joint comprising a ball portion and a cup portion said ball portion having an outer load bearing surface configured to engage with a load bearing surface within said cup potion;
    a ceramic treated with ion implantation, wherein said ion implanted ceramic is characterized as having a compressive stress in said surface due to said ion implantation wherein said ion-implanted ceramic with said compressive stress is not amorphous, wherein said ion implanted ceramic is said load bearing surface on at least one of said ball portion and said cup portion of said prosthetic joint.

11. The prosthesis of claim 10 wherein said ion implanted ceramic is on said ball portion of said prosthetic joint.

12. The prosthesis of claim 10 wherein said ion implanted ceramic is on said cup portion of said prosthetic joint.

13. The prosthesis of claim 10 wherein said ball and said cup portion each including load bearing surfaces defining a tensile stress, wherein at least one of said ball and said cup portions comprises said ion implanted ceramic having said compressive stress sufficient to counteract said tensile stress.

14. The prosthesis of claim 10 wherein said ion-implanted ceramic is further characterized as having a maximum compressive stress in said surface due to said ion implantation wherein said ceramic with said maximum compressive stress is not amorphous.

15. The prosthesis of claim 10, wherein said prosthetic joint comprises a knee joint, a finger joint, a toe joint, a shoulder joint, an arm joint, an elbow joint, a hip joint, an ankle joint, a neck joint, a spinal cord joint, and a combination thereof.

16. The prosthesis of claim 10, wherein the ceramic is selected from a group consisting of Alumina ($Al_2O_3$), Zirconia, Chromium Oxide ($Cr_2O_3$), Silicon Oxide ($SiO_2$) and a combination thereof.

17. The prosthesis of claim 10, wherein the ceramic treated with ion implantation comprises a ceramic treated at a concentration of about $1\times10^{17}$ ions per $cm^2$ or less.

18. The prosthesis of claim 10, wherein said ion implanted in said ceramic is selected from a group consisting of positive ions, nitrogen ions, calcium ions, hydrogen ions, boron ions, and a combination thereof.

19. The prosthesis of claim 10, further comprising a diamond-like coating on said ceramic.

20. The prosthesis of claim 19 wherein said diamond-like coating further comprises an amorphous and cross-linked carbon network and wherein said diamond-like coating includes inter-atomic bonds between said ceramic and said diamond-like coating.

* * * * *